United States Patent [19]

Stuchlik et al.

[11] Patent Number: 6,046,163
[45] Date of Patent: Apr. 4, 2000

[54] CYCLOSPORIN FORMULATION

[75] Inventors: Milan Stuchlik; Tomas Andrysek, both of Opava; Alexander Jegorov, Ceske Budejovice; Ales Husek, Opava; Vladimir Matha, Ceske Budejovice; Josef Stuchlik, Hrabvne, all of Czechoslovakia

[73] Assignee: Galena As, Opava, Czech Rep.

[21] Appl. No.: 09/101,653

[22] PCT Filed: Jan. 17, 1997

[86] PCT No.: PCT/GN97/00131

§ 371 Date: Nov. 23, 1998

§ 102(e) Date: Nov. 23, 1998

[87] PCT Pub. No.: WO97/26003

PCT Pub. Date: Jul. 24, 1997

[30] Foreign Application Priority Data

Jan. 18, 1996 [CS] Czechoslovakia ................. 169-96

[51] Int. Cl.[7] ................. A61K 38/00; A61K 31/33; A61K 31/34
[52] U.S. Cl. ................. 514/11; 514/183; 514/461
[58] Field of Search ................. 514/11, 183, 461

[56] References Cited

U.S. PATENT DOCUMENTS 5,589,455 12/1996 Woo .......................... 514/11

FOREIGN PATENT DOCUMENTS

| 0451461A2 | 10/1991 | European Pat. Off. . |
| 0650721A1 | 5/1995 | European Pat. Off. . |
| 0711550A1 | 5/1996 | European Pat. Off. . |
| 2636534 | 12/1990 | France . |
| 2228198A | 8/1990 | United Kingdom . |

*Primary Examiner*—Kevin E. Weddington
*Attorney, Agent, or Firm*—Beyer & Weaver, LLP

[57] ABSTRACT

Therapeutical compositions comprising from 0.1 to 20% by weight of a cyclosporin and a vehicle comprising from 1 to 60% by weight of polyethers constituted by, preferably, substances like ethoxy diglycol or polyethylene glycols 300 to 600 and/or substances like preferably dimethyl isosorbide, dimethyl isoidide and dimethyl isomannide, and from 1 to 60% by weight of a mixture of glyceryl monoesters of $C_8$–$C_{22}$ fatty acids and hexaglyceryl to pentadecaglyceryl monoesters of $C_8$–$C_{22}$ fatty acids in a ratio of 1:2 to 1:6. The therapeutical compositions preferably additionally comprise further adjuvants like anti-oxidants, preserving agents and stabilizers, flavoring agents, thickening agents and diluents. The compositions for external use preferably additionally comprise lipoaminoacids.

9 Claims, No Drawings

CYCLOSPORIN FORMULATION

This invention relates to a pharmaceutical formulation comprising a cyclosporin as active ingredient. The invention relates to formulations for internal use and also to topical formulations.

Cyclosporins are immunosuppressive cyclic undecapeptides which are used particularly in relation to organ transplants. Cyclosporins are also used for treatment of autoimmune diseases and inflammatory conditions such as arthritis and rheumatic diseases. Further applications include antiparasitic treatments and cancer therapy. Certain Cyclosporins which are devoid of immunosuppressive activity have been found to exhibit an inhibitory effect towards replication of the HIV-1 virus and these compounds can be employed in therapy for treatment and prevention of AIDS or AIDS related diseases.

A wide variety of cyclosporins has been identified. Cyclosporins are highly hydrophobic and are consequently difficult to formulate in dosage forms providing adequate bioavailability. Solubility of cyclosporins in water typically does not exceed 25 mg/l. The high lipophilicity of cyclosporins is indicated by the value of the partition coefficient P in the system n-octanol/water. For ciclosporin, values of log P=2.08 to 2.99 have been reported.

Dispersion systems characterised by the presence of a hydrophilic phase, a hydrophobic phase and a tensoactive component have been used to afford acceptable bioavailability for cyclosporin formulations. Commercially available compositions for oral administration are available under the trade marks Sandimmun, Sandimmun-Neoral, Consupren, Implanta and Imusporin. These formulations are disclosed in GB-A-2015339, GB-A-2222770, GB-A-2270842 and GB-A-2278780. A modification wherein the hydrophilic phase is omitted and replaced by partial esters of fatty acids with polyols such as propylene glycol, glycerol or sorbitol is disclosed in GB-A-2228198.

DE-A-4322826 discloses a carrier system for drugs which are poorly soluble in water, comprising a composition containing polyglyceryl esters of fatty acids as a co-tenside to non-ionic tensides having HLB higher than 10, in the presence of a triacyl glycerol as the lipophilic component. Use of dimethyl iso-sorbide as a co-tenside is mentioned in GB-A-650721.

Compositions for external treatment of inflammatory skin diseases containing, as accelerators of percutaneous absorption, a combination of N-acyl sarcosine and salts thereof with fatty acid amides prepared as reaction products of aliphatic carboxylic acids with mono- and di-ethanolamides are disclosed in JP-A2-07025784.

It has been surprisingly found that it is possible to prepare cyclosporin formulations having advantages over prior compositions by modification of the lipidic components and omission of ethyoxylated tensides from the formulation. While the solubility of cyclosporin in olive oil or corn oil does not exceed 50 mg/ml, we have discovered that solubility of cyclosporin in glyceryl monoesters is higher by approximately an order of magnitude.

According to the present invention a pharmaceutical composition containing cyclosporin for internal or external use is characterised in comprising from 0.1 to 20% by weight of a cyclosporin (I) and a vehicle comprising:

(i) from 1 to 60% by weight of at least one polyether (II) of a general formula IIa

(IIa)

wherein n is an integer from 2 to 20, R is H or $C_1$–$C_3$ alkyl, (ii) and/or a compound of general formula IIb

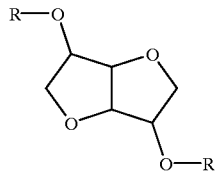

(IIb)

wherein R is $C_1$–$C_3$ alkyl;

(iii) and from 1 to 60% by weight of a mixture of one or more glyceryl monoesters of $C_8$–$C_{22}$ fatty acids (III) and one or more polyglyceryl esters selected from hexaglyceryl to pentadecaglyceryl monoesters of $C_8$–$C_{22}$ fatty acids (IV) in a ratio of components (III)/(IV) of 1:2 to 1:6.

We have found that mixtures of polar lipids formed by monoesters of fatty acids with glycerol and of pseudolipids formed by monoesters of fatty acids with polyglycerols for example from hexaglycerol to pentadecaglycerol are particularly suitable for formulation of cyclosporin.

Cyclosporins which may be employed comprise one or more of: ciclosporin, [NVa]²-ciclosporin, [MeIle]⁴ ciclosporin, [3'-O-acylMeBmt]¹-ciclosporin.

The polyether IIa is preferably selected from: ethoxy diglycol or polyethylene glycols 300 to 600.

The compound of formula IIb is preferably selected from dimethyl isoidide, dimethyl isomannide and, more preferably, dimethyl isosorbide.

The compound III is selected from: glyceryl monooctanoate, glyceryl monodecanoate, glyceryl monooleate and glyceryl monolinolate.

The compound IV is selected from polyglyceryl monoesters preferably one or more of: hexaglyceryl monooleate, octaglyceryl monostearate, octaglyceryl monooleate, decaglyceryl monolaurate, decaglyceryl monomyristate, decaglyceryl monostearate and decaglyceryl monooleate.

The compositions may include one or more adjuvants (V) for example antioxidants, preserving agents, stabilizers, flavouring agents, thickening agents and diluents.

Compositions in accordance with this matter which are intended for external use may include lipoaminoacids (VI), obtained by an acylation of aminoacids or of protein hydrolyzates with $C_8$–$C_{22}$ fatty acids. The weight ratio of the compounds (I)/(VI) is preferably 1:1 to 1:3.

The lipoaminoacids (VI) are preferably selected from capryloyl glycine, dicapryloyl cystine, dipalmitoyl hydroxyproline, lysine lauroyl methionate and dioctyldodecyl lauroyl glutamate.

The solvents from the group of polyethers serve to modify the physical characteristics of the formulation, especially in direct contact with the aqueous media of the gastro-intestinal tract or when diluting the concentrate before administration. The pharmacokinetic characteristics of compositions in accordance with the invention indicate reproducible absorption and good bioavailability.

Preferred compositions in accordance with this invention have as the vehicle lipids consisting of monoacyl glycerols wherein the acyl residue is $C_8$–$C_{22}$ and monoacyl glycerols with 6 to 15 glycerol units. Use of $C_{12}$–$C_{22}$ fatty acid monoglycerides is preferred although a proportion of shorter chain eg $C_8$–$C_{10}$ fatty acids may facilitate passage of the active composition through mucosal cells of the gastrointestinal tract into the blood stream. Advantageously, monoacyl glycerols used in the composition of this invention have a monoester content of at least 95%. Suitable products are for example commercial types of glyceryl monooleate (GMO, produced by Grindsted) having the following characteristics:

| fatty acids composition | DIMODAN ® GMO | DIMODAN ® GMO 90 |
|---|---|---|
| oleic | min 78% | min 92% |
| linoleic and linolenic | max 15% | — |
| linoleic | — | max 6% |
| saturated $C_{16}$, $C_{18}$, $C_{20}$ | max 10% | — |
| saturated $C_{16}$, $C_{18}$ | — | max 2% |
| free fatty acids cont | max 1.5% | max 0.5% |

Similar products produced by Eastman under the trade names Myverol® 18-99 (glyceryl monoleate) or Myverole® 18-92 (glyceryl monolinoleate) with a minimal content of 90% monoesters can also be used.

Further products which are suitable as the polar lipidic component are monesters of polyglycerols of general formula $$HOCH_2-CHOH-CH_2-(-O-CH_2-CHOH-CH_2)_N-O-CH_2-CHOH-CH_2OH$$

wherein x=3 to 12.

The polyglycerols are characterised by the following properties:

|  | mol weight | OH groups no | hydroxyl value |
|---|---|---|---|
| hexaglycerol | 462 | 8 | 970 |
| heptaglycerol | 536 | 9 | 941 |
| octaglycerol | 610 | 10 | 920 |
| nonaglycerol | 684 | 11 | 903 |
| decaglycerol | 758 | 12 | 880 |
| pentadecaglycerol | 1228 | 17 | 846 |

Esters of polyglycerols with fatty acids are generally prepared either by partial esterification of the polyglycerols with corresponding saturated or unsaturated fatty acids or by transesterification of vegetable oils with polyglycerol. Each individual monoester of polyglycerol is characterised by is saponification number, the polymerisation degree in turn is best indicated by the hydroxyl value. Monoesters of polyglycerols especially suitable for the compositions of the invention are the following:

| hexaglyceryl monooleate | NIKKOL ® HEXAGLYN 1 - 0 |
| octaglyceryl monosteatrate | SANTONE ® 8-1-S |
| octaglyceryl monoleate | SANTONE ® 8-1-0 |
| decaglyceryl monolaurate | NIKKOL ® DECAGLYN 1 - L |
| decaglyceryl monomyristate | NIKKOL ® DECAGLYN 1 - M |
| decaglyceryl monostearate | NIKKOL ® DECAGLYN 1 - S |
| decaglyceryl monooleate | NIKKOL ® DECAGLYN 1 - 0 |

These polyglycerol monoesters are commercialised under the trade mark NIKKOL® by Nikko Chemicals Co Ltd and under the trade mark SANTONE® by Durkee Foods.

The whole group of polyglycerol monesters, useful for the compositions of the invention, is characterised by the following purity tests:

| acid number | max 6 |
| heavy metals content | max 10 ppm |
| water content | max 2% |
| fatty acids Na salts content | max 2% (as Na stearate) |
| total ash | max 1% |

Preferred compositions may include cyclic ethers obtained by alkoxylation of anhydro derivatives of alcoholic hexoses for example sorbitol, mannitol and iditol. Anhydrisation of sorbitol or of other alcoholic hexoses occurs under catalytic action of concentrated sulphuric acid giving isosorbide (exo-endo)    isoidide (endo-endo)    isomannide (exo-exo)

A subsequent reaction with, for example, methyl chloride gives 2,5-di-O-methyl derivatives, which are useful as solvents for cyclosporin formulations. An especially suitable product is 2,5-dimethyl isosorbide, produced under the trade mark ARLASOLVE® DMI by ICI.

It was surprisingly found in studies of the solubility of ciclosporin in 2,5-dimethyl isosorbide that, dependent on the water content, the solubility of cyclosporin has an anomalous behaviour and reaches a maximal value at a molar fraction of N=0.5. The solubility of ciclosporin slightly decreases with increasing concentration of dimethyl isosorbide and only 324 mg $g^{-1}$ dissolves in the anhydrous product at 20° C. (see Table 1).

TABLE 1

Solubility of ciclosporin in a binary mixture 2,5-dimethyl isosorbide (DMI)/water

| Concentration of DMI Molar fraction, [N] | Weight/% | Solubility of ciclosporin [mg · $g^{-1}$] |
|---|---|---|
| 0.0 | 0.0 | 0.023 |
| 0.07 | 40 | 1.90 |
| 0.13 | 60 | 5.60 |
| 0.19 | 70 | 45.9 |
| 0.23 | 74 | 87.4 |
| 0.25 | 76 | 109.3 |
| 0.27 | 78 | 161.7 |
| 0.32 | 82 | 288.9 |
| 0.39 | 86 | 496.3 |
| 0.62 | 94 | 487.2 |
| 0.71 | 96 | 471.9 |
| 0.84 | 98 | 389.9 |
| 1.00 | 100 | 324.3 |

Ciclosporin forms, with 2,5-dimethyl isosorbide, a solvated form which crystallises in the monoclinic spatial group $P2_1$ with the following lattice parameters: a=15.521 (2)Å, b=20.833 (3)Å, c=12.223 (3)Å,β=100.21 °(1), Z=2 (Hušak M, Kratochvil B, Jegorov A, Maťha V, Stuchlik M, Andrysek T: The structure of a new cyclosporin A solvated form, Zeitschrift fur Kristallographie, 211, 313–318, 1996).

The improvement of the solubility of ciclosporin in binary systems dimethyl isosorbide-water has a clear advantage when formulating soft gelatine capsules where migration of water from the gelatine layer into the mass of the capsule occurs.

A polyether from the group of general formula II especially preferred for the composition of the invention is ethoxy diglycol, known in the pharmaceutical trade under the trade name TRANSCUTOL® and commercialised by the French firm Gattefosse.

The solubility of cyclosporin in ethoxy diglycol alone is 578.5 mg.g$^{-1}$ at 20° C. and is influenced in an insubstantial way by a small amount of water. Ciclosporin dissolves in a binary mixture of ethyoxy diglycol with water at a concentration of ethoxy diglycol corresponding to a molar fraction of N=0.5, 216 mg.g$^{-1}$ at 20° C.

Ethoxy diglycol which is preferred for use in accordance with this invention has the following physical and chemical characteristics:

| density | 0.88–0.989 |
| --- | --- |
| refractive index | 1.425–1.429 |
| boiling point | 295–202° C. |
| acid value | max 0.1 |
| peroxide value | max 12.5 |
| water content | max 0.1 |
| heavy metals content | max 10 ppm |

Products from the group of polyethers of general formula IIa, also suitable for the compositions of the invention, are liquid to semi-solid polyethylene glycols having an average molecular weight of 200 to 600. These polyethers tend to form supersaturated solutions with cyclosporins, from which non-solvated orthorhombic forms may crystallise. Stabilisation of these polyethylene glycol solutions is enabled by adding a small amount of propylene glycol, as is demonstrated in Table 2.

TABLE 2

Solubility of ciclosporin in binary mixture polyethylene glycol/propylene glycol

| Concentration of PEG 400 | | Solubility of ciclosporin |
| --- | --- | --- |
| Molar fraction [N] | weight [%] | [mg · g$^{-1}$] |
| 0.0 | 0.0 | 214.5 |
| 0.021 | 10.0 | 186.1 |
| 0.045 | 20.0 | 194.5 |
| 0.059 | 25.0 | 182.1 |
| 0.11 | 40.0 | 186.2 |
| 0.16 | 50.0 | 182.4 |
| 0.22 | 60.0 | 189.0 |
| 0.31 | 70.0 | 185.6 |
| 0.36 | 75.0 | 182.7 |
| 0.43 | 80.0 | 183.6 |
| 0.63 | 90.0 | 172.9 |
| 1.0 | 100.0 | 131.2 |

TABLE 3

Physical and chemical characteristics of polyethylene glycols preferred for use in compositions of the invention

| | hydroxyl value | density [g/cm$^3$] | viscosity [mPa · s] | solidification point [° C.] |
| --- | --- | --- | --- | --- |
| PEG 200 | 534–591 | 1.124 | 60–70 | −50 |
| PEG 300 | 356–394 | 1.125 | 85–100 | −15—10 |
| PEG 400 | 267–295 | 1.126 | 110–125 | 4–8 |
| PEG 600 | 178–197 | 1.126 | 16–19* | 17–22 |
| PEG 1000 | 107–118 | 1.200 | 24–29* | 35–40 |

*50% aqueous solution

For the compositions of the invention intended for external application to the skin and mucous membranes the vehicle as described above may be complemented with lipoaminoacids. These function as biovectors allowing passage through the skin and fixing the aminoacids in the upper layers of the epidermis. By their ampiphilic structure lipoaminoacids may be incorporated into the intercellular tissue and may play an important role in cohesion properties of corneocytes, and may thus contribute to the working of the hydroregulation and barrier function of the skin. By means of their bioaffinity to the skin lipoaminoacids may regulate the speed of penetration of the vehicle containing dissolved cyclosporin to the site of effect. The carboxyl functions of the lipoaminoacids are regulators of the desired pH reaction of the skin, thus contributing to the therapeutic effect of the immunomodulating drug.

Especially preferred lipoaminoacids are non-ionic derivatives of an N-acyl glutamic acid and higher fatty alcohols like, eg dioctyldodecyl lauroyl glutamate eg Amiter LGOD (trade mark of Ajinmoto) as a pseudolipidic component compatible with monoesters of glycerol.

Other suitable lipoaminoacids for topical compositions of the invention are, eg, capryloyl glycine, dicapryloyl crystine, dipalmitoyl hydroxyproline, lysine lauroyl methionate, or N-acyl derivatives of aminoacids prepared from protein hydrolyzates like collagen or milk or wheat proteins. These products are commercialised, eg under the trade mark LIPACID® by the French firm Seppic.

This invention is further described by means of example but not in any limitative sense.

Example 1

Soft Gelatine Capsules

The following ingredients were used.

| (I) | ciclosporin | 10.00 g |
| --- | --- | --- |
| (IIb) | dimethyl isosorbide | 30.00 g |
| (III) | glyceryl monooleate | 15.00 g |
| (IV) | decaglyceryl monooleate | 44.40 g |
| (V) | tocopherol linoleate | 0.60 g |

The ingredients (III), (IV) and (IIb) were mixed at 50° C. To the resulting mixture, (I) and an anti-oxidating additive (V) were added and the mixture was stirred until dissolution under a blanket of an inert gas. The resulting product was filtered and filled into soft gelatine capsules.

| (I) | ciclosporin | 10.00 g |
| --- | --- | --- |
| (IIa) | polyethylene glycol 400 | 40.00 g |
| (III) | glyceryl monooleate | 10.00 g |
| (IV) | decaglyceryl monooleate | 30.00 g |
| (V) | propylene glycol | 9.40 g |
| (V) | neohesperidine dihydrochalcone | 0.20 g |
| (V) | tocopherol R,R,R-α | 0.40 g |

The ingredients (III), (IV) and (IIa) were mixed at 50° C. To the resulting mixture, (I) a mixture of adjuvants (V) was added. The resultant mixture was stirred until dissolution under a blanket of an inert gas. The resulting product was filtered and filled into glass vials.

EXAMPLE 3

Ointment for External Use

An ointment with the following composition was prepared.

| (I)   | ciclosporin                    | 3.00 g  |
|-------|--------------------------------|---------|
| (IIa) | ethoxy diglycol                | 12.00 g |
| (III) | glyceryl monolinolate          | 62.00 g |
| (IV)  | decaglyceryl monolaurate       | 16.00 g |
| (VI)  | di-octyldodecyl lauroyl glutamate | 5.00 g |
| (VI)  | caproyl glycine                | 2.00 g  |

Substances (III), (IV), (V), (VI) were melted at 50° C. and mixed together. Substance (I) was dissolved individually in (II) and the resulting solution was homogenized with the melt and filled into suitable containers allowing external application.

The ointment was tested in comparison with a placebo. Albinotic guinea pigs were used for testing. The animals were sensitized at the bases of both ears with 50 µl of 5% dinitrofluorobenzene (DNFB) and repeatedly with 2% DNFB dissolved in a 1:1 mixture acetone/olive oil. After 6 days the animals were shaved and epilated on both sides. On the following day, 20 µl of 0.5% dinitrofluorobenzene dissolved in a 1:1 mixture acetone/olive oil was applied to both sides. Immediately after this application, 250 mg of the composition of Example 3 was applied to the right side of the guinea pig and 250 mg of the placebo composition of Example 3 to the left side of the guinea pig. Two control groups of the animals were used in testing the composition.

Negative control: the animals obtained 20 µl of 0.5% dinitrofluorobenzene to both side.

Positive control: the animals were not treated with the tested composition.

Erythemas at 24 and 32 hours after application of the compositions were evaluated.

Scale for evaluating erythema:

4-dark red protruding stain 3-red stain 2-rose coloured stain 1-small spots 0-without any visible change

|         | animals | Evaluation of erythema: | | | |
|---------|---------|---------|---------|---------|---------|
|         |         | 5% DNFB | | 2% DNFB | |
|         | number  | 24 h    | 32 h    | 24 h    | 32 h    |
| comp of ex 3 | 5 | *0.2 0.05 | *0.2 0.05 | **0 | **0 |
| placebo, ex 3 | 5 | 1.3 1.03 | 1.1 0.64 | 1.7 0.82 | 1.3 1.3 |
| negat control | 5 | 0 | 0 | 0.2 0.05 | 0.2 0.06 |
| posit control | 5 | 2.49 0.52 | 2.1 0.88 | 2.2 0.63 | 1.5 0.71 |

\*- p < 0.01
\*\*- p < 0.001

The importance was evaluated by student's t-test against the placebo composition.

Evaluation of oedema was obtained by reading the values of skin thickness [mm] one day before application and the values of skin thickness at 8, 24, 32 and 48 h after application.

| | number of animals (pieces) | 8 h | 24 h | 32 h | 48 h |
|---|---|---|---|---|---|
| | | | [mm] | | |
| comp of ex 3 | 5 | 0.11 | 0.42 | 0.33 | 0.24 |
| placebo, ex 3 | 5 | 0.35 | 0.63 | 0.63 | 0.49 |
| negat control | 5 | 0.15 | 0.24 | 0.17 | 0.08 |
| posit control | 5 | 0.20 | 0.44 | 0.35 | 0.19 |

EXAMPLE 4

Hard Gelatine Capsules

The following ingredients were used.

| (I)   | [NVa]$^2$-ciclosporin    | 15.00 g |
|-------|--------------------------|---------|
| (IIb) | dimethyl isosorbide 95%  | 35.00 g |
| (III) | glyceryl monocaprinate   | 5.00 g  |
| (III) | glyceryl monolinolate    | 12.00 g |
| (IV)  | octaglyceryl monostearate | 32.60 g |
| (V)   | tocopherol R,R,R-α       | 0.40 g  |

Substances (IV) and (III) were melted at 50° C., mixed together and an anti-oxidant (V) added. To the resulting mixture a solution of (I) n (IIb) was added, homogenised and the product after filtration was filled into hard gelatine capsules at 50° C.

| (I)   | ciclosporin                 | 10.0 g |
|-------|-----------------------------|--------|
| (II)  | 2,5-dimethyl isosorbide (95%) | 30.0 g |
| (III) | glyceryl monooleate         | 20.0 g |
| (IV)  | hexaglyceryl monoleate      | 40.0 g |

The composition was filled into starch capsules CAPILL to give 50 mg cyclosporin in each capsule.

Pharmacokinetic evaluation of the composition and comparison with the commercial product was carried out after administering a single dose of 100 mg of cyclosporin in a two-phase cross-over experiment on 10 Beagle dogs. Male dogs of the age of 12 to 36 months and weighing 9 to 13 kg were fed a standard pelleted diet in the amount of 300 g daily, with water ad libitum.

The composition was administered after starving for 18 hr. Further food was given to the animals after an interval of 10 hr. Blood was taken from the forearm vein in the intervals 0, 0.5, 1, 2, 3, 5 and 8 hr. The blood samples were frozen at −20° C. for storage prior to analysis of the cyclosporin content by liquid chromatography. Pharmacokinetic parameters were calculated by 1 compartment analysis using the programme KIN FIT and are as follows:

| | | $AUC_{0-8h}$ [h · mg · l$^{-1}$] | $AUC_{0-\infty}$ [h · mg · l$^{-1}$] | $T_{½E1}$ [h] | Tmax [h] | Cmax [mg − 1$^{-1}$] |
|---|---|---|---|---|---|---|
| comp of ex 1 | Ø | 2.474 | 4.274 | 4.822 | 1.953 | 0.465 |
|              | SD | 1.022 | 2.037 | 1.994 | 1.505 | 0.157 |
| commerc comp | Ø | 2.900 | 3.687 | 2.890 | 1.493 | 0.735 |
|              | SD | 0.534 | 0.900 | 1.024 | 0.812 | 0.260 |

Explanation of abbreviations:
AUC area under curve
$T_{½E1}$ elimination half-time
Tmax time of attaining maximal concentration
Cmax maximal concentration
SD standard deviation
Ø average concentration

EXAMPLE 6

Oral Solution

The following ingredients were used.

| | | |
|---|---|---|
| (I) | ciclosporin | 10.00 g |
| (IIa) | polyethylene glycol 400 | 19.70 g |
| (III) | glyceryl monooleate | 16.10 g |
| (IV) | decaglyceryl monoolaurate | 43.90 g |
| (V) | propylene glycol | 10.00 g |
| (V) | hesperidine dihydrochalcone | 0.30 g |

Ingredients (III), (IV) and (IIa) were mixed together at 50° C. Ciclosporin (I) and both additives (V) were added and the mixture was stirred until dissolution of (II) under an inert gas blanket. The resultant mixture was filtered and filled into glass vials with gas-tight seals.

Pharmacokinetic evaluation of the composition of Example 6 in comparison with the commercial composition CONSUPREN solution was made in 10 Beagle dogs. Males aged two years and of a weight of 13 to 16.5 kg were fed with a standard feed with free access to water. Single administrations of both tested and compared compositions were made after 18 hr starvation. Further feed was given to the animals only after taking blood sample after 12th hour of administration. Blood was taken from the forearm vein in the intervals of 0, 1, 2, 3, 5, 3, 12 and 24 hr. The blood samples were stored at −20° C. prior to analysis using the RIA kit by IMMUNOTECH for ciclosporin and its metabolites.

Individual blood levels (ng/ml) after single administration of 100 mg ciclosporin

COMPOSITION OF EXAMPLE 6

| time | 1 hr | 2 hr | 3 hr | 5 hr | 8 hr | 12 hr | 24 hr | $AUC_{0-24}$ |
|---|---|---|---|---|---|---|---|---|
| levels of | 141 | 883 | 1423 | 997 | 683 | 498 | 189 | 10659 |
| individual | 1648 | 1631 | 1068 | 755 | 491 | 329 | 110 | 10382 |
| subjects | 1244 | 1316 | 1018 | 685 | 515 | 391 | 143 | 9719 |
| | 1601 | 2000 | 1564 | 1021 | 677 | 498 | 152 | 13160 |
| | 1634 | 1250 | 884 | 664 | 454 | 328 | 96 | 10850 |
| | 774 | 1604 | 1388 | 830 | 514 | 356 | 116 | 11779 |
| | 50 | 1245 | 1208 | 765 | 534 | 384 | 108 | 15765 |
| | 1462 | 1309 | 1046 | 656 | 449 | 290 | 85 | 11588 |
| | 561 | 945 | 897 | 764 | 768 | 356 | 92 | 10609 |
| | 1444 | 1447 | 1030 | 567 | 369 | 267 | 73 | 11878 |
| mean | 1055.9 | 1363 | 1152.6 | 770.4 | 545.4 | 369.7 | 116.4 | 11638.7 |
| SD | 592.12 | 313.00 | 221.36 | 138.23 | 118.14 | 73.65 | 33.52 | 1653.13 |

REFERENCE COMPOSITION CONSUPREN SOLUTIO

| time | 1 hr | 2 hr | 3 hr | 5 hr | 8 hr | 12 hr | 24 hr | $AUC_{0-24}$ |
|---|---|---|---|---|---|---|---|---|
| levels of | 502 | 972 | 860 | 667 | 454 | 338 | 91 | 9271 |
| individual | 125 | 613 | 1153 | 1377 | 1172 | 830 | 300 | 18452 |
| subjects | 470 | 563 | 833 | 899 | 617 | 374 | 123 | 10420 |
| | 267 | 964 | 1144 | 1479 | 922 | 559 | 166 | 15340 |
| | 379 | 1028 | 898 | 601 | 380 | 244 | 73 | 7977 |
| | 221 | 816 | 1380 | 1372 | 640 | 769 | 242 | 16381 |
| | 461 | 1113 | 1440 | 863 | 638 | 413 | 137 | 12251 |
| | 216 | 743 | 706 | 503 | 278 | 250 | 76 | 6705 |
| | 726 | 1136 | 909 | 750 | 558 | 335 | 116 | 10430 |
| | 463 | 1315 | 1263 | 678 | 545 | 408 | 140 | 11379 |
| mean | 383 | 926.3 | 1058.6 | 918.9 | 620.4 | 452 | 146.4 | 11860.25 |
| SD | 169.12 | 227.96 | 238.66 | 340.06 | 246.62 | 193.68 | 69.38 | 3589.88 |

SD - standard deviation
$AUC_{0-24}$ area under curve

What is claimed is:

1. A pharmaceutical composition containing cyclosporin for internal or external use, characterized in comprising from 0.1 to 20% by weight of a cyclosporin (I), and a vehicle comprising:
(i) from 1 to 60% by weight of at least one polyether (II) of a general formula IIa $$R-O-(CH_2CH_2O-)_nH \qquad (IIa)$$

wherein n is an integer from 2 to 20, R is H or $C_1-C_3$ alkyl, (ii) and/or a compound of general formula IIb

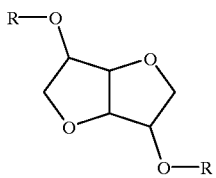

(IIb)

wherein R is $C_1$–$C_3$ alkyl;
(iii) and from 1 to 60% by weight of a mixture of one or more glyceryl monoesters of $C_8$–$C_{22}$ fatty acids (III) and one or more polyglyceryl esters selected from hexaglyceryl to pentadecaglyceryl monoesters of $C_8$–$C_{22}$ fatty acids (IV) in a ratio of components (III)/(IV) of 1:2 to 1:6.

2. A pharmaceutical composition as claimed in claim 1, characterized in that the cyclosporin (I) is selected from: cyclosporin, [NVa]$^2$-cyclosporin, [MeIle]$^4$-cyclosporin and [3'-O-acylMeBmt]$^1$-cyclosporin.

3. A pharmaceutical composition as claimed in claim 1 characterized in that the compound of formula IIa is selected from: ethoxy diglycol or polyethylene glycols 300 to 600.

4. A pharmaceutical composition as claimed in claim 1, wherein the compound of formula IIb is selected from: dimethyl isosorbide, dimethyl isoidide and dimethyl isomannide.

5. A pharmaceutical composition as claimed in claim 1, characterized in that the compounds III are selected from: glyceryl monooctanoate, glyceryl monodecanoate, glyceryl monooleate and glyceryl monolinolate.

6. A pharmaceutical composition as claimed in claim 1, wherein the compounds IV are selected from: hexaglyceryl monooleate, octaglyceryl monostearate, octaglyceryl monooleate, decaglyceryl monolaurate, decaglyceryl monomyristate, decaglyceryl monostearate and decaglyceryl monooleate.

7. A pharmaceutical composition according to claim 1, further comprising one or more adjuvants (V) selected from: anti-oxidants, preserving agents, stabilizers, flavoring agents, thickening agents and diluents.

8. A pharmaceutical composition for external use as claimed in claim 1, wherein the vehicle includes one or more lipoaminoacids (VI), obtained by an N-acylation of aminoacids or of protein hydrolyzates with $C_8$–$C_{22}$ fatty acids; the weight ratio of the compounds (I)/(VI) being 1:1 to 1:3.

9. A pharmaceutical composition as claimed in claim 8, characterized in that lipoaminoacids (VI) are selected from: capryloyl glycine, dicapryloyl cystine, dipalmitoyl hydroxyproline, lysine lauroyl methionate and di-octyldodecyl lauroyl glutamate.

* * * * *